United States Patent
Lin et al.

(10) Patent No.: US 11,062,444 B2
(45) Date of Patent: Jul. 13, 2021

(54) ARTIFICIAL INTELLIGENCE CATARACT ANALYSIS SYSTEM

(71) Applicant: Zhongshan Ophthalmic Center of Sun Yat-sen University, Guangdong (CN)

(72) Inventors: Haotian Lin, Guangdong (CN); Xiaohang Wu, Guangdong (CN); Weiyi Lai, Guangdong (CN)

(73) Assignee: ZHONGSHAN OPHTHALMIC CENTER OF SUN YAT-SEN UNIVERSITY, Guangdong (CN)

( * ) Notice: Subject to any disclaimer, the term of this patent is extended or adjusted under 35 U.S.C. 154(b) by 84 days.

(21) Appl. No.: 16/535,760

(22) Filed: Aug. 8, 2019

(65) Prior Publication Data
US 2020/0294225 A1 Sep. 17, 2020

(30) Foreign Application Priority Data

Mar. 12, 2019 (CN) .......................... 201910184479.1

(51) Int. Cl.
G06K 9/00 (2006.01)
G06T 7/00 (2017.01)
(Continued)

(52) U.S. Cl.
CPC .......... *G06T 7/0012* (2013.01); *A61B 3/1176* (2013.01); *G06K 9/00536* (2013.01);
(Continued)

(58) Field of Classification Search
CPC ......... G06T 7/0012; G06T 2207/20081; G06T 2207/30041; G06N 20/00; A61B 3/1176;
(Continued)

(56) References Cited

U.S. PATENT DOCUMENTS

2003/0025876 A1* 2/2003 Nanjo ..................... A61B 3/12
351/206
2004/0004694 A1* 1/2004 Sugino .................... A61B 3/14
351/206
(Continued)

OTHER PUBLICATIONS

Pritam et al, (Sensitivity and specificity of automated analysis of single-field non-mydriatic fundus photographs by Bosch DR Algorithm-Comparison with mydriatic fundus photography (ETDRS) for screening in undiagnosed diabetic retinopathy, PLoS ONE 12 (12): e0189854. https://doi.org/10.1371/journal. (Year: 2017).*

*Primary Examiner* — Amara Abdi
(74) *Attorney, Agent, or Firm* — Muncy, Geissler, Olds and Lowe, P.C.

(57) ABSTRACT

The invention relates to an artificial intelligence cataract analysis system, including a pattern recognition module for recognizing a photo mode of an input eye image, wherein the photo mode is divided according to the slit width of the illuminating slit during photographing of the eye image and/or whether a mydriatic treatment is carried out; a preliminary analysis module used for selecting a corresponding deep learning model for eye different photo modes, analyzing the characteristics of lens in the eye image by using a deep learning model, and further performing classification in combination with cause and severity degree of a disease. The invention can perform cataract intelligent analysis on eye images with different photo modes by using deep learning models, so that the analysis accuracy is improved.

14 Claims, 2 Drawing Sheets

(51) Int. Cl.
*G06N 20/00* (2019.01)
*A61B 3/117* (2006.01)

(52) U.S. Cl.
CPC .... *G06N 20/00* (2019.01); *G06T 2207/20081* (2013.01); *G06T 2207/30041* (2013.01)

(58) Field of Classification Search
CPC .... A61B 3/0025; A61B 3/14; G06K 9/00536; G06K 9/6292; G06K 9/00604; G06K 9/6267; G06K 2009/00583; G06K 9/00577
See application file for complete search history.

(56) References Cited

U.S. PATENT DOCUMENTS

| | | | |
|---|---|---|---|
| 2008/0234144 A1* | 9/2008 | Ho | G01N 33/54326 506/39 |
| 2017/0000342 A1* | 1/2017 | Samec | A61B 3/10 |
| 2018/0206717 A1* | 7/2018 | Ramesh Kumar | A61B 3/102 |
| 2020/0211235 A1* | 7/2020 | Hsu | G06T 11/001 |

* cited by examiner

| Grade | Color | Examples of cataract types |
|---|---|---|
| I | Transparent or gray | Cortical or subcapsular opacity type |
| II | Gray or gray yellow | posterior subcapsular opacity type |
| III | Yellow or light brown | Advanced senile cataract |
| IV | Deep yellow or amber | Nuclear senile cataract |
| V | Dark brown or black | "Persistent" cataract |

ARTIFICIAL INTELLIGENCE CATARACT ANALYSIS SYSTEM

TECHNICAL FIELD

The invention relates to the technical field of medical image processing equipment, in particular to an artificial intelligence cataract analysis system.

BACKGROUND ART

Cataracts are the number one cause of blindness, and China has the largest number of cataract patients with over 70 million people. At present, cataract extraction surgery is the only effective way of treatment, and timely diagnosis and surgical treatment can help patients avoid blindness.

However, the current cataract diagnosis relies on a limited number of professional ophthalmologists. The data published by the International Council for Ophthalmology (ICO) in 2012 shows that the number of certified Chinese ophthalmologists is only 28,338 with only 1 ophthalmologist per 60,000 people, which had not reached the goal put forward by the World Health Organization in the "VISION 2020" initiative of having 1 ophthalmologist per 50,000 people in Asia till 2020. Meanwhile, the regional distribution of the ophthalmologists is extremely uneven. 70% of the national ophthalmologists are distributed in large and medium-sized cities and are concentrated in the regional grade-A tertiary hospitals with low coverage of community people, which is far from meeting the needs of the cataract patients with huge base and rapid growth.

The artificial intelligence provides a possibility for solving the supply-and-demand contradiction of medical resources, but the existing artificial intelligence system only performs intelligent analysis on patients with specific types of eye images captured in specified mode, or the analysis accuracy rate is rather low. Moreover, the existing artificial intelligence system can only be used on the premise of screening the patients in advance in a large hospital by a specialist doctor or a technician, which cannot be popularized to the primary hospitals due to the lack of ophthalmologists and medical resources. Therefore, the difficulty in hospitalizing patients cannot be truly solved, and the cataract diagnosis coverage rate cannot be fundamentally improved.

SUMMARY OF THE INVENTION

The invention aims to overcome at least one defect (deficiency) of the prior art, and provides an artificial intelligence cataract analysis system which can perform cataract intelligent analysis on eye images of different photo modes by using different deep learning models, so that the analysis accuracy is higher.

The invention adopts a technical scheme as follows.

An artificial intelligence cataract analysis system, including a pattern recognition module used for recognizing a photo mode of an input eye image, wherein the photo mode is divided according to the slit width of a slit lamp during the photographing of the eye image and/or whether a mydriatic treatment is carried out; and a preliminary analysis module used for selecting a corresponding deep learning model for eye images of different photo modes, and classifying the images based on the characteristics of lens in the eye image by using the deep learning model.

The clinical analysis of cataracts depends on ophthalmic professional equipment, the slit lamp, to acquire the situation of lens by means of photographing the anterior segment of the eye. However, various slit lamp photos can be divided into mydriatic photographing and small pupil photographing according to whether the patient has been performed mydriatic treatment before photographing; and can be divided into slit light photographing and diffused light photographing according to the width of the illuminating slit. The eye images taken in different photo modes have a marked difference in the forms of eyeball and lens. When the deep learning method is applied to eye image analysis, the accuracy of analysis can be quite low if the training set contains different photo modes and a unified deep learning model is used to classified and analyzed these images. Therefore, the input eye image is recognized about the photo mode in the pattern recognition module. Then a first deep learning model corresponding to the identified photo mode is selected with pertinence in the preliminary analysis module, and the cataract classification and analysis is performed by using the selected first deep learning model. Therefore, the accuracy of the cataract intelligent analysis of different photo modes is improved.

Further, the preliminary analysis module is used for the classification based on the characteristics of the lens by using the first deep learning model. And the classification includes normal lens, the lens with cataract, and the lens after cataract extraction surgery.

Further, the system also includes an evaluation analysis module used for classifying cataractous images as congenital cataract and acquired cataract according to the input ages.

Further, the evaluation analysis module is also used for classifying the eye images, which have been classified as congenital cataract, as the non-visual axis region opacification and the visual axis region opacification based on the characteristics of the visual axis region in the eye image.

Further, the evaluation analysis module is also used for classifying the eye images, which have been classified as acquired cataract, as nucleus hardness I-II and nucleus hardness III-V based on the characteristics of the lens nucleus in the eye image.

Further, the evaluation analysis module is also used for classifying the eye images, which have been classified as the nucleus hardness I-II, as the non-capsular opacification and the subcapsular opacification based on the characteristics of the lens capsule in the eye image.

Further, the evaluation analysis module is also used for screening out the eye images of posterior subcapsular opacification from the eye images after cataract extraction surgery, based on the characteristics of the posterior capsule in the eye image.

Further, the evaluation analysis module is also used for classifying the eye images, which have been screened out to be posterior subcapsular opacification after cataract surgery, as the non-visual axis region opacification and the visual axis region opacification based on the characteristics of the visual axis region in the eye image.

Further, the step in which the pattern recognition module is used for identifying the photo mode of the input image, and/or the step in which the evaluation analysis module is used for classifying the eye images as the non-visual axis region opacification and the visual axis region opacification based on the characteristics of the visual axis region in the eye image, and/or the step in which the evaluation analysis module is used for classifying the eye images as nucleus hardness I-II and nucleus hardness III-V based on the characteristics of the lens nucleus in the eye image, and/or the step in which the evaluation analysis module is used for classifying the eye images as the non-capsular opacification and the subcapsular opacification based on the characteristics of the lens capsule in the eye image, and/or the step in which the eye image of posterior subcapsular opacification is screened out based on the characteristics of the posterior capsule in the eye image after cataract surgery; these steps specifically adopt a deep learning method.

Further, the system also includes a referral recommendation module used for generating a referral recommendation when the eye image is classified as having a visual axis region opacification or a subcapsular opacification or a nucleus hardness of III-V.

Compared with the prior art, the present invention has the following beneficial effects:

(1) The present invention performs the photo mode identification on the input eye image, and performs cataract intelligent analysis on the recognized different photo modes by using different deep learning models, so that the accuracy can be improved;

(2) The present invention integrates a plurality of modules with analysis function including the preliminary analysis module and the evaluation analysis module, which intelligentize an early screening and the intermediate analysis link of the cataract;

(3) The present invention utilizes the deep learning method, so that the accuracy of the early screening and the intermediate analysis of the cataract are higher;

(4) The present invention also integrates the referral recommendation module, by which a trained technician only needs to input the eye image into the invention and can obtain a referral recommendation through analysis, so that the heavy work of early screening and intermediate analysis link of the cataract sink to the primary hospitals, and the workload of the professional ophthalmologist is reduced.

DESCRIPTION OF EMBODIMENTS

Figure 1:
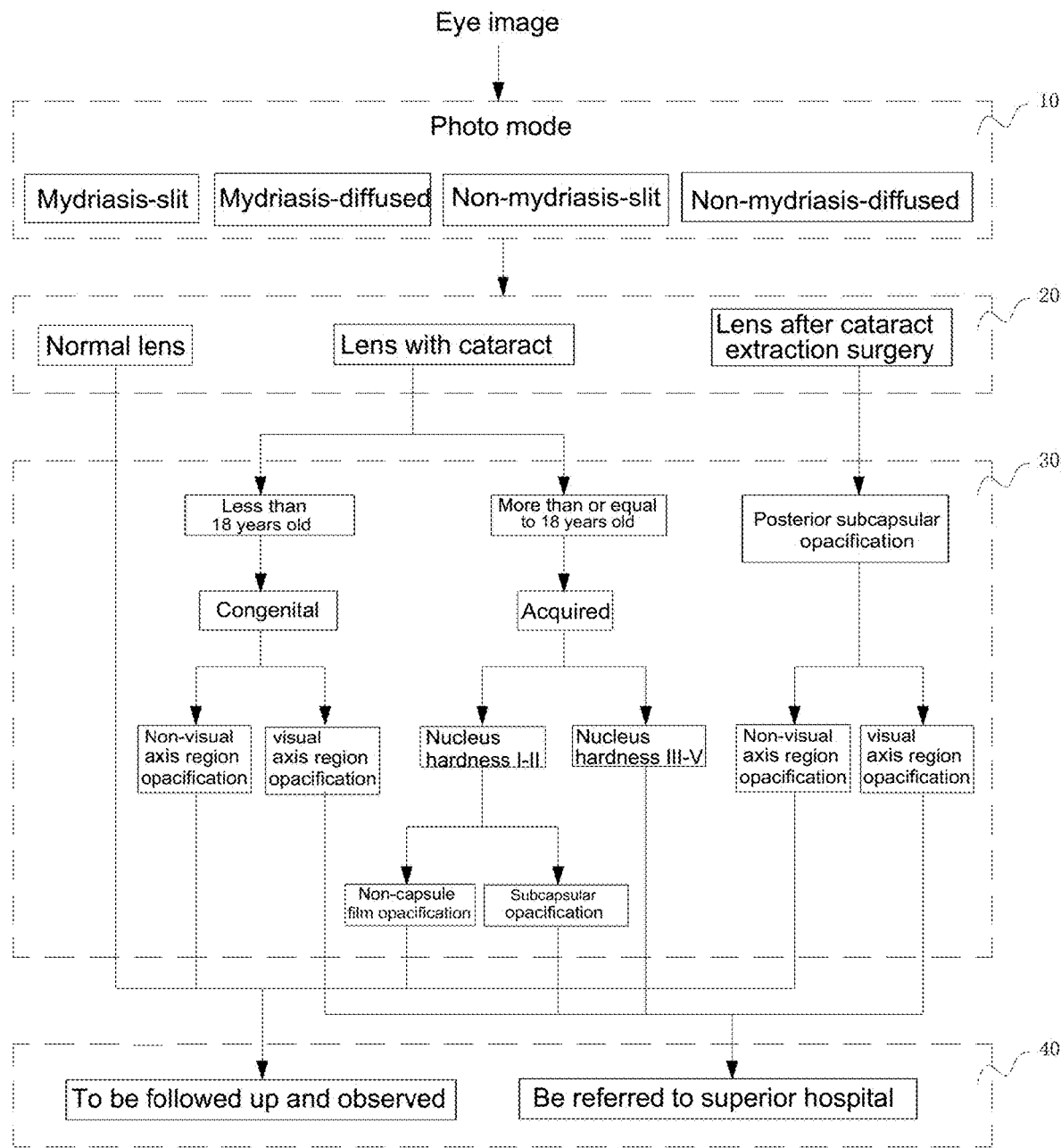
FIG. 1 is a schematic diagram of an analysis process according to an embodiment of the present invention.

The drawings are for illustrative purposes only and are not to be construed as limiting the invention. Some components in the drawings are omitted, enlarged, or reduced to better illustrate the following embodiments, and sizes of these components do not represent sizes of actual products. It will be appreciated by those skilled in the art that some known structures and descriptions thereof may be omitted.

Embodiment

As shown in FIG. 1, the present embodiment provides an artificial intelligence cataract analysis system, includes a pattern recognition module 10 used for recognizing a photo mode of an input eye image, wherein the photo mode is divided according to the slit width of a slit lamp during the photographing of the eye image and/or whether a mydriatic treatment is carried out; and a preliminary analysis module 20 used for selecting different first deep learning models for eye images of different photo modes, and classifying the images based on the characteristics of the lens in the eye image by using the first deep learning model.

The clinical analysis of cataracts depends on ophthalmic professional equipment, the slit lamp, to acquire the situation of the lens by means of photographing the anterior segment of the eye. However, various slit lamp photos can be divided into mydriatic photographing and small pupil photographing according to whether the patient has been performed mydriatic treatment before photographing; and can be divided into slit light photographing and diffused light photographing according to the width of the slit lamp. The diameter of the pupil in a natural state is 2 to 3 mm, and is dilated to over 5 mm by the mydriatic treatment using a cycloplegic agent, so that the periphery of the lens can be comprehensively observed. The slit light photographing section is convenient to observe the lens, eyeball structure and lesion depth, and the diffused light photographing can comprehensively observe the ocular surface structure.

The width of the illuminating slit and whether the mydriatic treatment is performed are combined, and the photo mode can be divided into a mydriasis-slit mode, a mydriasis-diffused mode, a non-mydriasis-slit mode and a non-mydriasis-diffused mode.

The eye images taken in different photo modes have a marked difference in the forms of eyeball and lens. When the deep learning method is applied to eye image analysis, the accuracy can be quite low if the training set contains different photo modes and a unified deep learning model is used to classify and analyze these eye images. Therefore, the input eye image in the pattern recognition module 10 is identified about the photo mode. A first deep learning model corresponding to the identified photo mode is selected with pertinence in the preliminary analysis module 20, and the cataract classification and analysis is performed by using the selected first deep learning model, so that the accuracy of cataract intelligent analysis is improved.

In a specific implementation of the embodiment, the pattern recognition module 10 is used for identifying the photo mode of the input eye image, and the step specifically adopts a deep learning method. The pattern recognition module 10 can adopt a second deep learning model to identify the photo mode of the input eye image, and the can lead to a higher recognition accuracy of the photo mode.

In the present embodiment, the preliminary analysis module 20 is used for the classification based on the characteristics of the lens in the eye image by using the first deep learning model, and the step specifically includes a classification of normal lens, the lens with cataract, and the lens after cataract extraction surgery based on the characteristics of the lens.

The preliminary analysis module 20 can classify eye images of different photo modes into normal lens, the lens with cataract (opacified lens), and the lens after cataract extraction surgery through different first deep learning models, which helps a professional ophthalmologist to further analyze the cataract and lays a foundation for further intelligent analysis of the system.

In this embodiment, the system further includes the evaluation analysis module 30 used for classifying the cataractous eye images as congenital cataract and acquired cataract according to the input ages.

In the preliminary analysis module 20, whether a cataractous image is congenital cataract or acquired cataract can be further determined according to the input ages in the evaluation analysis module 30. Taking 18 years old as a boundary line, the input eye image is classified as congenital cataract if the input age is less than 18 years old, and classified as acquired cataract if the input age is greater than or equal to 18 years old.

In the present embodiment, the evaluation analysis module 30 is also used for classifying the eye images, which have been classified as congenital cataract, as the non-visual axis region opacification and the visual axis region opacification based on the characteristics of the visual axis region in the eye image.

In the evaluation analysis module 30, if the input eye image is classified as congenital cataract, it can be further analyzed whether the visual axis region in the eye image is opacified, so as to evaluate the severity of the congenital cataract. The visual axis region refers to an area within a diameter range of 3 mm and is centered on the center of the eye. If it is analyzed that the visual axis region has opacification, it indicates an impaired vision, which is more severe.

In the specific implementation of the present embodiment, the evaluation analysis module 30 is used for classifying the eye image as the non-visual axis region opacification and the visual axis region opacification based on the characteristics of the visual axis region in the eye image, and this step specifically adopts a deep learning method. The evaluation analysis module 30 can classify the eye images, which have been classified as congenital cataract, as the non-visual axis region opacification and the visual axis region opacification by using a third deep learning model based on the characteristics of the visual axis region. The classification result can have higher accuracy by means of the third deep learning model.

In the present embodiment, the evaluation analysis module 30 is also used for classifying the eye images, which have been classified as acquired cataract, as nucleus hardness I-II and nucleus hardness III-V based on the characteristics of the lens nucleus in the eye image.

Figures 2, 3:
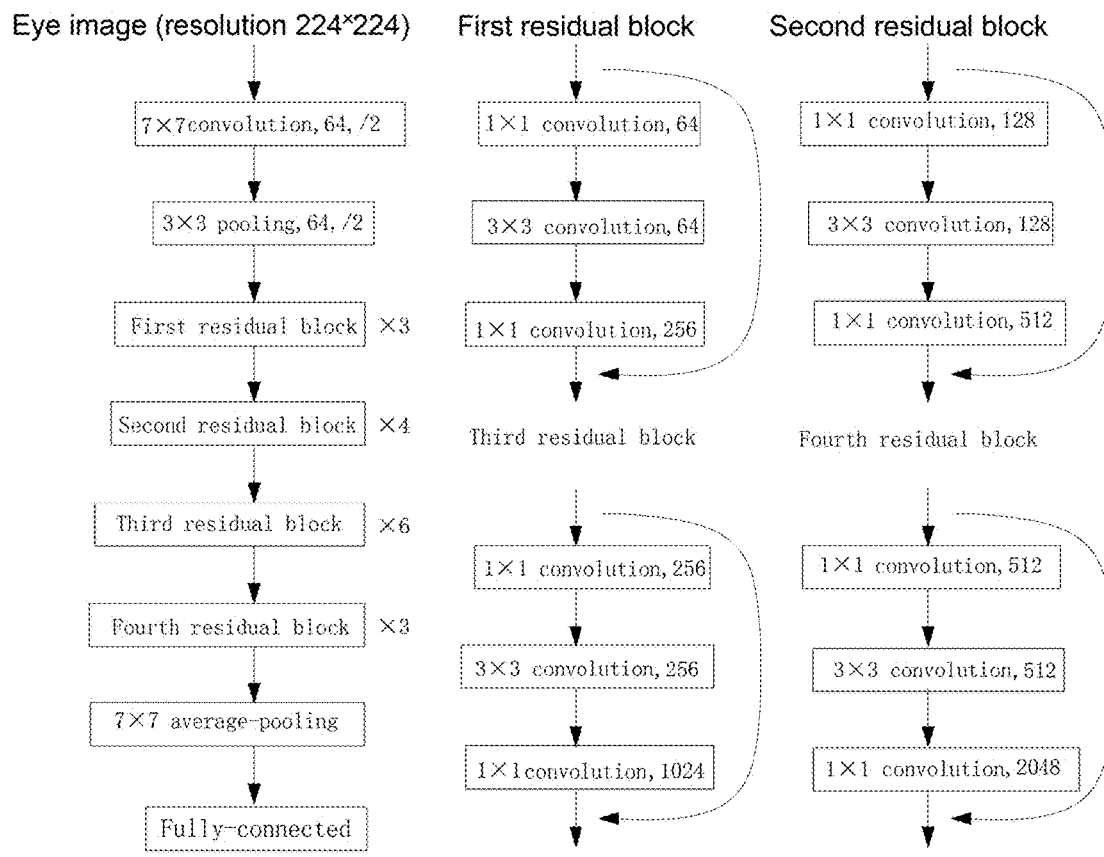
FIG. 2 is a schematic diagram of the nucleus hardness grade of the cataract according to the embodiment of the present invention.
FIG. 3 is a schematic diagram for establishing a deep learning model of the present invention.

In the evaluation analysis module 30, if the input eye image is classified as acquired cataract, the severity of acquired cataract can then be further evaluated by analyzing the characteristics of the lens nucleus in the eye image. As shown in FIG. 2, the color of the lens nucleus is different due to the grades of different lens nuclei. If it is analyzed that the eye image belongs to the nucleus hardness III-V, it indicates that the cataract is relatively more severe.

In the specific implementation of the present embodiment, the evaluation analysis module 30 is used for classifying the eye images as nucleus hardness I-II and nucleus hardness III-V based on the characteristics of the lens nucleus in the eye image, and this step specifically adopts a deep learning method. The evaluation analysis module 30 can classify the eye images, which have been classified as acquired cataract, as nucleus hardness I-II and nucleus hardness III-V by using a fourth deep learning model based on the characteristics of the lens nucleus in the eye image. The classification result can have higher accuracy by means of the fourth deep learning model.

In the present embodiment, the evaluation analysis module 30 is also used for classifying the eye images, which have been classified as nucleus hardness I-II, as the non-capsular opacification and the subcapsular opacification based on the characteristics of the lens capsule.

In the evaluation analysis module 30, if the input eye image is classified as nucleus hardness I-II, the severity of the acquired cataract of the nucleus hardness I-II can be further evaluated by analyzing whether the lens capsule in the eye image has opacification. If the subcapsular opacification is analyzed, it indicates that the cataract is relatively more severe.

In the specific implementation of the present embodiment, the evaluation analysis module 30 is used for classifying the eye images as the non-capsular opacification and the subcapsular opacification based on the characteristics of the lens capsule, and this step specifically adopts a deep learning method. The evaluation analysis module 30 can classify the eye images, which have been classified as nucleus hardness I-II, as the non-capsular opacification and the subcapsular opacification by using a fifth deep learning model based on the characteristics of the lens capsule in the eye image. The accuracy of classification can be higher by means of the fifth deep learning model.

In the present embodiment, the evaluation analysis module 30 is also used for screening out the eye images of posterior subcapsular opacification from the eye images after cataract extraction surgery based on the characteristics of the posterior capsule.

In preliminary analysis module 20, the eye image after cataract extraction surgery can be analyzed in the evaluation analysis module 30 that whether the subcapsular opacification exists in the eye image by the sixth deep learning model, so as to evaluate whether an after-cataract exists.

In a specific embodiment of the present embodiment, the evaluation analysis module 30 is used for screening out the eye image of posterior subcapsular opacification based on the characteristics of the posterior capsule, and this step specifically adopts a deep learning method. The evaluation analysis module 30 can screen out the eye image of posterior subcapsular opacification from the eye images after cataract extraction surgery by using a sixth deep learning model based on the characteristics of the posterior capsule in the eye image. The accuracy of classification can be higher by means of the sixth deep learning model.

In the present embodiment, the evaluation analysis module 30 is also used for classifying the eye images, which have been screened out as that of posterior subcapsular opacification, as the non-visual axis region opacification and the visual axis region opacification based on the characteristics of the visual axis region in the eye image.

In the evaluation analysis module 30, if the input eye image is screened out as that of posterior subcapsular opacification, or evaluated as having after-cataract, the severity of the after-cataract can then be further evaluated by analyzing whether the visual axis region in the eye image is opacified. If it is analyzed that the visual axis region has opacification, it indicates that the after-cataract affects the vision, which is more severe.

In the specific implementation of the present embodiment, the evaluation analysis module 30 is used for classifying the eye images as the non-visual axis region opacification and the visual axis region opacification based on the characteristics of the visual axis region in the eye image, and the step specifically adopts a deep learning method. The evaluation analysis module 30 can screen out the eye image of visual axis region opacification from the eye images which have been classified as posterior subcapsular opacification by using a seventh deep learning model based on the characteristics of the posterior capsule in the eye image. The accuracy of classification can be higher by means of the seventh deep learning model.

Further, the system also includes a referral recommendation module 40 used for generating a referral recommendation when the eye image is classified as having a visual axial region opacification or a subcapsular opacification or a nucleus hardness of III-V.

If the eye image is classified as having the visual axis region opacification, it indicates that the congenital cataract or the after-cataract has affected the vision. If the eye image is classified as nucleus hardness III-V, it indicates that the acquired cataract has been severe. If the eye image is classified as having subcapsular opacification, it indicates that there is a tendency of disease exacerbation although the type of the acquired cataract is nucleus hardness I-II. In the above situations, a referral recommendation is generated to allow the patient to be referred in time to a hospital with professional ophthalmologists.

If not, the system can generate a follow-up recommendation for the patient to be followed up and observed.

Preferably, the above-mentioned first deep learning model to the seventh deep learning model can use a CS-ResCNN (cost-sensitive residual convolutional neural network). The CS-ResCNN can cope with the classification problem of unbalanced medical data sets, thereby ensuring that the classification result is not inclined to major classes, and ensuring the classification accuracy of a minor class.

For eye images of different photo modes, different stages of the eye images can be classified by using the same third deep learning model to the seventh deep learning model respectively, or using a different third deep learning model to the seventh deep learning model respectively. For example, for the eye image in which the photo mode is a mydriasis-slit mode and has been classified as congenital cataract, the evaluation analysis module 30 can perform a classification of whether the visual axial region is opacified by using the third deep learning model corresponding to the mydriasis-slit mode. For the eye image in which the photo mode is a non-mydriasis-slit mode and has been classified as the eye image of congenital cataract, the evaluation analysis module 30 performs a classification of whether the visual axis region is opacified by using the third deep model corresponding to the non-mydriasis-slit mode. The third deep learning model corresponding to the mydriasis-slit mode used a training set composed of mydriasis-slit mode photos, and the third deep model corresponding to the non-mydriasis-slit mode used a training set composed of non-mydriasis-slit mode photos.

As shown in FIG. 3 in a specific implementation, the CS-ResCNN model includes a convolution layer, a pooling layer, a plurality of residual blocks, an average-pooling layer, and a fully-connected layer. When the resolution of the input eye image is 224×224, the convolution layer can use a 7×7 convolution kernel, and the pooling layer can use a 3×3 pooling kernel. As shown in FIG. 3, "7×7 convolution, 64, /2" in FIG. 3 represents a 7×7 convolution kernel, 64 number of channels, and the image output after passing through the convolution layer will be downsampled by 2×2 times; and "3×3 pooling, 64, /2" represents a 3×3 pooling kernel, 64 number of channels, and the image output after passing through the pooling layer is downsampled by 2×2 times. Then the image output after passing through the pooling layer passes through three first residual blocks, four second residual blocks, six third residual blocks and three fourth residual blocks, and the average-pooling layer with a 7×7 pooling kernel, and finally enters the fully-connected layer; wherein all the first residual blocks to the fourth residual blocks adopt a "bottleneck" residual block, and "1×1 convolution, 64" represents a 1×1 convolution kernel, and 64 number of channels, and so on.

The loss function expression of the CS-ResCNN model is:

$$L(w) = -\frac{1}{m}\left[\sum_{j=1}^{m}\sum_{t=1}^{k}\text{weight}\{y_j = t\}^* \log \frac{e^{kw_j^T x_j}}{\sum_{s=1}^{k} e^{kw_s^T x_j}}\right] + \frac{\lambda}{2}\sum_{j=1}^{k}\sum_{q=1}^{n} kw_{iq}^2$$

In the expression, weight$\{y_j=t\}$ represents the weight of the tth class, $$\frac{\lambda}{2}\sum_{i=1}^{k}\sum_{q=1}^{n} kw_{iq}^2$$

represents a penalty item that prevents over-fitting, wherein $$\frac{\lambda}{2}$$

are the weights of the penalty item, x represents the input image, y represents the corresponding category, kw is a hyperparameter reflecting the weight and bias value, k is the number of categories that need to be classified in a classification problem, and n is the number of neurons in the CS-ResCNN model.

The present embodiment integrates four function modules, including the pattern recognition module 10, the preliminary analysis module 20, the evaluation analysis module 30, and the referral recommendation module 40, which enable the analysis of cataracts to form an intelligent one-stop service, and intelligentize the early screening and the intermediate analysis link of the cataract. The trained technician can input eye images into each module in the embodiment, and obtain a referral recommendation, so that the method can be popularized and used in the primary hospitals lack of professional ophthalmologists, and the workload of the professional ophthalmologist can be reduced.

Obviously, the foregoing embodiments of the present invention are merely example for clear illustration of the technical scheme in the invention, and are not intended to limit the specific embodiments of the present invention. Any modification, equivalent substitution or improvement, and the like within the spirit and principle of the claims of the present invention should be included in the scope of claims of the present invention.

The invention claimed is:

1. An artificial intelligence cataract analysis system, comprising:
    a pattern recognition module used for recognizing a photo mode of an input eye image, wherein the photo mode is divided according to a slit width of an illuminating slit during photographing and/or whether a mydriatic treatment is carried out; and
    a preliminary analysis module used for selecting a corresponding deep learning model for different photo modes and classifying input eye images based on a characteristics of lens.

2. The artificial intelligence cataract analysis system according to claim 1, wherein the preliminary analysis module, which is used for a classification based on the characteristics of the lens in the eye image by using the deep learning model, specifically includes the classification of a normal lens, the lens with cataract, and the lens after cataract extraction surgery.

3. The artificial intelligence cataract analysis system according to claim 2, further comprising an evaluation analysis module used for classifying cataractous images as congenital cataract and acquired cataract according to input ages.

4. The artificial intelligence cataract analysis system according to claim 3, wherein the evaluation analysis module is also used for classifying the eye images, which have been classified as congenital cataract, as non-visual axis region opacification and visual axis region opacification based on the characteristics of a visual axis region in the eye image.

5. The artificial intelligence cataract analysis system according to claim 3, wherein the evaluation analysis module is also used for classifying the eye images, which have been classified as acquired cataract, as nucleus hardness I-II and nucleus hardness III-V based on the characteristics of the lens nucleus in the eye image.

6. The artificial intelligence cataract analysis system according to claim 5, wherein the evaluation analysis module is also used for classifying the eye images, which have been classified as the nucleus hardness I-II, as non-capsular opacification and subcapsular opacification based on the characteristics of the lens capsule in the eye image.

7. The artificial intelligence cataract analysis system according to claim 2, wherein the evaluation analysis module is also used for screening out the eye image of posterior subcapsular opacification from the eye images, which have been classified as the eye images after cataract extraction surgery, based on the characteristics of a posterior capsule in the eye image.

8. The artificial intelligence cataract analysis system according to claim 7, wherein the evaluation analysis module is also used for classifying the eye images, which have been screened out to be the posterior subcapsular opacification, as the non-visual axis region opacification and the visual axis region opacification based on the characteristics of the visual axis region in the eye image.

9. The artificial intelligence cataract analysis system according claim 1, wherein the step in which the pattern recognition module is used for identifying the photo mode of the input eye image specifically adapts the deep learning model.

10. The artificial intelligence cataract analysis system according to claim 1, further comprising a referral recommendation module used for generating a referral recommendation when the eye image is classified as having a visual axial region opacification or a subcapsular opacification or a nucleus hardness of III-V.

11. The artificial intelligence cataract analysis system according claim 4, wherein the step in which the evaluation analysis module is used for classifying the eye images as the non-visual axis region opacification and the visual axis region opacification based on the characteristics of the visual axis region in the eye image specifically adapts the deep learning model.

12. The artificial intelligence cataract analysis system according claim 5, the step in which the evaluation analysis module is used for classifying the eye images as a nucleus hardness I-II and a nucleus hardness III-V based on the characteristics of the lens nucleus in the eye image specifically adapts the deep learning model.

13. The artificial intelligence cataract analysis system according claim 6, the step in which the evaluation analysis module is used for classifying the eye images as the non-capsular opacification and the subcapsular opacification based on the characteristics of the lens capsule in the eye image specifically adapts the deep learning model.

14. The artificial intelligence cataract analysis system according claim 7, the step in which the eye image of posterior subcapsular opacification is screened out from postoperative images based on the characteristics of the posterior capsule in an ocular image specifically adapts the deep learning model.

* * * * *